United States Patent [19]

Godfrey et al.

[11] Patent Number: 4,745,068

[45] Date of Patent: May 17, 1988

[54] DISPERSION TOOL

[75] Inventors: Otis W. Godfrey, Greenwood; Walter A. Raas, Brownsburg; James R. Ayres, Indianapolis, all of Ind.

[73] Assignee: Eli Lilly and Company, Indianapolis, Ind.

[21] Appl. No.: 44,150

[22] Filed: Apr. 30, 1987

[51] Int. Cl.[4] .................. C12M 1/02

[52] U.S. Cl. .................. 435/316; 366/266; 366/270

[58] Field of Search .................. 435/299, 305, 311, 315, 435/316, 286; 366/266, 270; 241/246

[56] References Cited

U.S. PATENT DOCUMENTS

| | | | |
|---|---|---|---|
| 1,864,149 | 6/1932 | Rockwell | 366/266 |
| 1,926,446 | 9/1933 | Klosson | 366/270 |
| 1,982,002 | 11/1934 | Hatch | 366/270 |
| 2,038,221 | 4/1936 | Kagi | 366/266 |
| 2,530,814 | 11/1950 | De Becze et al. | 435/315 |
| 2,793,166 | 5/1957 | Hatch | 435/315 |
| 3,137,481 | 6/1964 | MacLean | 366/266 |
| 4,307,846 | 12/1981 | Spelsberg | 241/246 |
| 4,441,824 | 4/1984 | Brokaw | 366/266 |

*Primary Examiner*—James C Yeung

*Attorney, Agent, or Firm*—Barnes & Thornburg

[57] ABSTRACT

A device for homogenizing a liquid containing a mixture of single cells and cell clusters is provided. The device includes a shroud for channeling the liquid and suspended particles. The shroud defines an inner bore that is formed to include an axial inlet opening and at least one spaced apart outlet opening. A homogenizing bit is provided that is disposed within the inner bore for dispersing the suspended particles in the liquid to form a homogenized substance. The bit includes a shear blade fixed to the bit at a location near the axial inlet opening, with the shear blade configured to cooperate with adjacent shear ports to shear a portion of the suspended particles. The bit also includes a spiral portion that is configured to draw the liquid and suspended particles axially into and through the inner bore from the inlet opening.

13 Claims, 1 Drawing Sheet

DISPERSION TOOL

BACKGROUND AND SUMMARY OF THE INVENTION

The present invention relates to tools for dispersing various substances in a liquid. More particularly, the present invention relates to a tool that is powered by an air motor and that is adapted to disperse biological samples in relatively small liquid batches and to blend or homogenize the sample.

In order to produce certain types of biochemical Products, it is known to create a fermentation broth in which microorganisms are reproduced. These growing microorganisms create various fermentation products in a known manner. Many of the desired fermentation products created by the growing of microorganisms in a fermentation broth are contained either within the cell wall of the individual microorganism, or are attached to the cell wall of the microorganism. In order to recover these products, it is normally desirable to expose the individual microorganisms to an appropriate solution or solvent.

The exposure of the cells is generally accomplished by homogenizing the mixture of cells with a dispersion tool. An appropriate solvent can be added to the liquid dispersion to aid in extracting the desired fermentation product or compound. The solvent is generally selected depending upon the solubility of the product or compound of interest, such that the desired product or compound can be uniformly dispersed in suspension. The selection of the appropriate solvent is known by those skilled in the art, and will not be discussed further here.

Conventional dispersion tools for homogenizing such a cell dispersion are generally driven by electric motors. These motors are generally very bulky, at least for the horsepower generated, and generally create a considerable amount of heat due to friction.

One problem with the conventional dispersion tools is that, because the drive motors create a considerable amount of heat, the heat is transmitted through the dispersion tool to the cell dispersion. Because many types of biological products and compounds are extremely temperature sensitive, this excess heat has the potential for destroying many of the desired compounds and products. In addition, the excess heat reduces the life expectancy of both the dispersion tool and the motor.

Another problem with the conventional dispersion tools is that the drive motors frequently create sparks. This creates the potential to ignite the solvent in the cell dispersion where flamible solvents are employed.

According to the present invention, a device for homogenizing a liquid containing a plurality of suspended particles is provided. The device includes a shroud for channeling the liquid and suspended particles. The shroud defines an inner bore that is formed to include an axial inlet opening and at least one spaced apart outlet opening. A dispersion bit is provided that is disposed within the inner bore for manipulating the liquid and suspended particles to form a homogenized substance. The bit includes a shear blade attached to the bit at a location near the inlet opening, with the shear blade configured to cooperate with shear outlet openings to shear a portion of the suspended particles. The bit also includes a spiral portion that is configured to draw the liquid and suspended particles axially into and through the inner bore from the inlet opening.

One feature of the foregoing structure is that the bit is configured to include both a shear blade and a spiral portion. One advantage of this feature is that the shear blade acts to shear a portion of the suspended particles in the liquid. In addition, the spiral portion acts to create an upward pumping motion for the liquid and suspended particles which assures recycling of heavier particulate material through the dispersion tool.

In preferred embodiments of the present invention, the inner bore is divided into a first chamber and a separate second chamber. In addition, the bit is configured to include an outwardly extending flange that cooperates with a chamfer on the inner bore to sealingly separate the first chamber from the second chamber. One advantage of this feature is that the liquid to be homogenized is not permitted to enter the second chamber. This is advantageous because the second chamber of the inner bore is configured to accommodate the attachment end of the air motor, which is ideally isolated from any of the liquid to be homogenized.

Also in preferred embodiments of the present invention, the shroud is configured to include additional secondary outlet openings spaced apart from the primary outlet openings. One advantage of this feature is that, by providing both primary and secondary outlet openings for the shroud, and specifically from the first chamber, the liquid and suspended particles that are being pumped into the first chamber are permitted to escape through the two sets of outlet openings to provide for complete circulation of the liquid and suspended particles.

Also in preferred embodiments of the present invention, the shroud is configured to include vent outlets to permit venting of the second chamber. One advantage of this feature is that by providing vent outlets from the second chamber, it is possible to introduce air into the second chamber which exits through the vent openings. This enables the second chamber to be pressurized slightly, which aids in preventing any of the liquid or suspended particles from entering the second chamber.

Thus, the dispersion device of the present invention provides for improved homogenization of a fermentation product without introducing any significant heat into the suspension. The tool is driven by an air motor, which permits unattended operation of the tool without the chance of solvent fires. The tool is capable of performing the dispersion operation more efficiently and in a shorter period of time than was heretofore possible.

Additional objects, features, and advantages of the invention will be apparent to those skilled in the art upon consideration of the following detailed description of a preferred embodiment exemplifying the best mode of carrying out the invention as presently perceived.

DETAILED DESCRIPTION OF THE DRAWINGS

Figure 1:
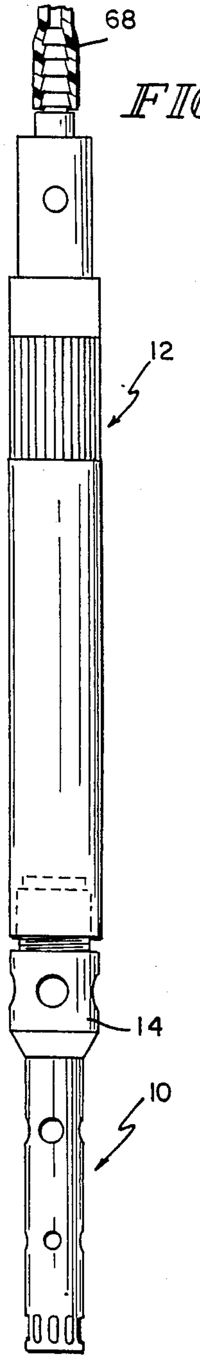
FIG. 1 is a side elevational view showing the dispersion tool of the present invention attached to an air driven motor.

Referring now to FIG. 1, FIG. 1 shows a tool 10 according to the present invention. The tool 10 is shown in a use configuration attached to an air driven motor 12. Illustratively, in the preferred embodiment, the air driven motor 12 is a model 10R0400A 18 produced by Dotco. The motor 12 is configured to rotate at a speed of between 40,000 and 60,000 RPM. Air for driving the motor 12 is provided by an air hose 68.

Figure 2:
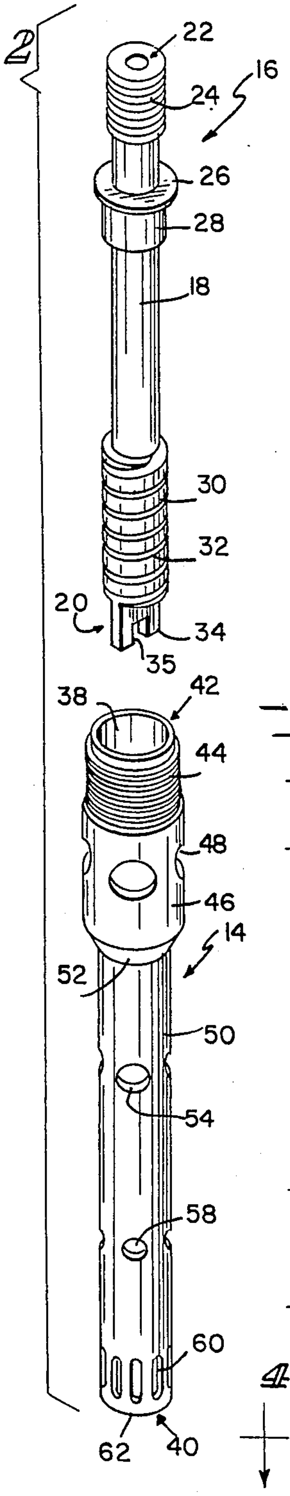
FIG. 2 is an exploded view of the tool shown in FIG. 1.

Referring now to FIG. 2, FIG. 2 shows the tool 10 in greater detail. The tool 10 consists of two separate components, an outer shroud 14 and a dispersion bit 16. The dispersion bit 16 includes an elongated shaft 18 having a first end 20 and a second end 22. A threaded portion 24 is formed adjacent the second end 22. As will be discussed later, the threaded portion 24 is provided to permit engagement with a portion of the air motor 12 in order to impart rotational movement to the bit 16. An outwardly extending flange 26 is disposed on the shaft 18 at a location spaced apart from the threaded portion 24. A collar 28 is provided on the shaft 18 adjacent the flange 26. A spiral portion 30 is provided on the shaft 18 at a location spaced apart from the collar 28. The spiral portion 30 includes a spiral groove 32 that extends entirely around the spiral portion 30 from one end of the spiral portion 30 to the other end. A generally flat, H-shaped shear blade 34 is provided on the first end 20 of the shaft 18 and includes a notch 35 centrally situated on a lower surface of the blade 34.

The shroud 14 is a generally cylindrically-shaped, hollow member formed to include an inner bore 38. The inner bore 38 is sized and shaped to receive the bit 16. The shroud 14 has a first end 40 and a second end 42. A threaded portion 44 is formed adjacent the second end 42. The threaded portion 44 is provided to permit engagement of the air motor 12 to the shroud 14. An enlarged diameter drive area 46 is provided near the second end 42. Four vent outlets 48 are provided in the drive area 46. The vent outlets 48 are spaced around the outer circumference of the drive area 46 and extend radially into the inner bore 38. A reduced diameter portion 50 is provided that extends from the drive area 46 to the first end 40. An outer chamfer 52 provides the demarcation between the drive area 46 and the reduced diameter portion 50.

Four secondary outlet openings 54 are provided on the portion 50 intermediate the outer chamfer 52 and the first end 40. Like the vent outlets 48, the secondary outlet openings 54 are spaced around the outer circumference of the portion 50 and extend radially into the inner bore 38. In addition, four primary outlet openings 58 are provided on the portion 50 that are located intermediate the secondary outlet openings 54 and the first end 40. As will be described below, the diameter of the primary outlet openings 58 is slightly smaller than the diameter of the secondary outlet openings 54. Eight side openings or shear ports 60 are formed in the portion 50 substantially near the first end 40. The shear ports 60 are generally oblong-shaped openings that are spaced around the outer circumference of the portion 50. In addition, the first end 40 is open to provide a bottom inlet opening 62 (best shown in FIGS. 3 and 4).

Although it will be understood that the dimensions of both the bit 16 and shroud 14 are interrelated in that the shroud 14 is sized to receive the bit 16 for rotation therein, the dimensions of both the bit 16 and shroud 14 could be changed to accommodate different uses. Therefore, the dimensions given for both the bit 16 and shroud 14 are for illustrative purposes only, and are illustrative only the dimensions of the preferred embodiment that is illustrated in the drawings. Referring to FIG. 1, the overall length of the combined air tool 12 and dispersion tool 10 is approximately 8.5 inches (21.6 cm.). Referring to FIG. 2, the bit 16 has a length from the first end 20 to the second end 22 of approximately 2.43 inches (6.18 cm.). The shear blade 34 has a length of 0.225 inches (0.570 cm.), which gives the bit 16 an overall length of 2.66 inches (6.75 cm.). The flange 26 has a diameter of 0.335 inches (0.850 cm.) and the collar 28 has a diameter of 0.245 inches (0.620 cm.). The shaft 18 has a diameter of 0.180 inches 0.450 cm.). The spiral portion 30 has a diameter of 0.250 inches ( 0.630 cm.) and a length of 0.60 inches (1.52 cm.). The width of the shear blade 34 is substantially equal to the diameter of the spiral portion 30.

Referring now to the shroud 14, the shroud 14 has an overall length from the first end 40 to the second 42 of 2.97 inches (7.54 cm.). The spacing between the vent outlets 48 and the secondary outlet openings 54 is 0.89 inches (2.26 cm). The spacing between the secondary outlet openings 54 and the primary outlet openings 58 is 0.735 inches (1.86 cm.). The spacing between the primary outlet openings 58 and the shear ports 60 is 0.60 inches (1.52 cm.). The inner bore 38 within the reduced diameter portion 50 has an inside diameter of 0.260 inches (0.660 cm.). The diameter of the vent openings 48 is 0.190 inches (0.480 cm.). The diameter of the secondary outlet openings 54 is 0.155 inches (0.390 cm.). The diameter of the primary outlet opening 58 is 0.125 inches (0.310 cm.). The dimension of each shear port 60 is 0.064 inches (0.160 cm.) in width and 0.183 inches (0.464 cm.) in length.

Figure 3:
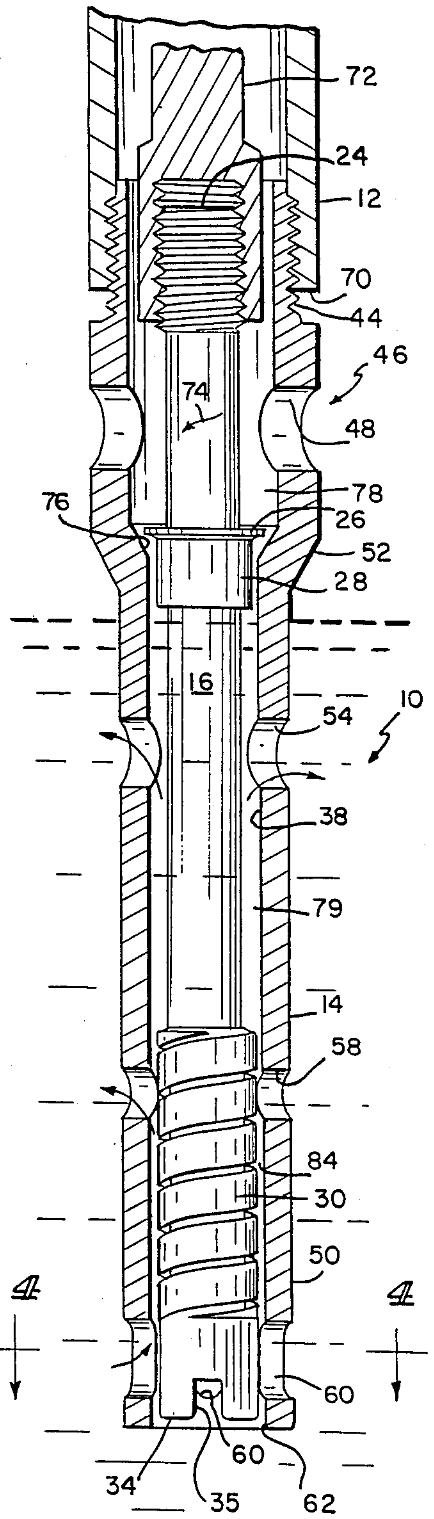
FIG. 3 is a transverse sectional view of the tool shown in FIG. 2.

Referring now to FIG. 3, FIG. 3 shows the assembled dispersion tool 10 with the bit 16 fitted within the inner bore 38 of the shroud 14. To join the air motor 12 to the shroud 14, the threaded end 44 of the shroud 14 is engaged with a threaded end 70 of the motor 12. The threaded end 24 of the bit 16 is threadingly engaged with an air motor drive shaft 72 that is located within the threaded end 70 of the motor 12. It will be understood that the drive shaft 72 provides rotational movement to the bit 16 in a conventional manner. As discussed previously, the drive shaft 72 normally rotates the bit 16 within the shroud 14 at a speed of between 40,000 and 60,000 RPM. The direction of rotation of the bit 16 is indicated by an arrow 74.

The inner bore 38 of the shroud 14 is formed to include an inner chamfer 76 that basically corresponds to the outer chamfer 52. The inner chamfer 76 effectively divide the inner bore 38 into an axially lower, first chamber 79 and an axially upper, second chamber 78. As seen in FIG. 3, when the bit 16 is inserted into the shroud 14, the flange 26 and collar 28 are situated adjacent the inner chamfer 76. The flange 26 and collar 28 are sized to remain out of contact with the inner surfaces of the inner bore 38, however the clearances between the inner bore and these elements are minimal. These minimal clearances permit the flange 26 and collar 28 to cooperate with the inner chamfer 76 to partially seal the second chamber 78 from the first chamber 79. However, the clearances are large enough to prevent the liquid from being drawn into the second chamber 78 due to capillary action.

The spiral portion 30 and shear blade 34 are both sized to provide a clearance space 84 between the outer surface of both the spiral portion 30 and the shear blade 34 and the inner bore 38. Illustratively, in the preferred embodiment, the difference in the inner diameter of the inner bore 38 and the outer diameter of the spiral portion 30 and shear blade 34 is 0.010 inches (0.025 cm.). Because the bit 16 is centered within the inner bore 38 and the shroud 14, this provides a clearance space 84 equal to one-half of the difference in these diameters, or 0.005 inches (0.013 cm.).

Figure 4:
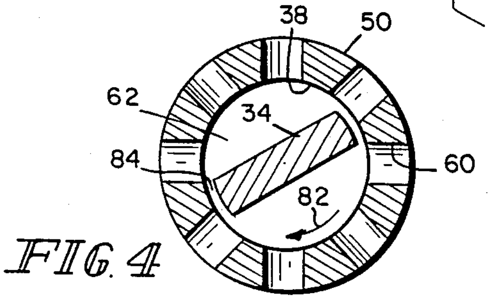
FIG. 4 is a sectional view taken along lines 4—4 of FIG. 3.

FIG. 4 shows a cross-sectional view of a lower portion of the reduced diameter portion 50, and particularly shows the orientation of the shear blade 34 with respect to the shear ports 60. FIG. 4 also illustrates the clearance space 84 between the edges of the shear blade 34 and the inner bore 38.

In operation, the dispersion tool 10 is normally utilized to resuspend and homogenize a cellular mass in a liquid to expose the maximum surface of the individual microorganisms in the sample. This exposure is necessary to permit the subsequent optimal release of desired compounds and products from the microorganisms. It will be understood that the suspension tool 10 of the present invention is also capable of dispersing other types of substances. Referring to FIG. 3, the tool 10 is attached to an air motor 12 that is used to rotate the bit 16 at a speed of between 40,000 and 60,000 RPM within the shroud 14. Normally, a manifold containing a plurality of tools 10 is utilized, with the plurality of tools lowered into a similar plurality of vessels (not shown) containing the material sought to be dispersed. An appropriate solvent may be added to the vessel during the homogenization.

After the air motor 12 is supplied with air through the air hose 68 to begin rotating the bit 16, the liquid and suspended microorganisms (not shown) are drawn into the inner bore 38 through the bottom inlet opening 62. The majority of the microorganisms are sheared immediately by the shear blade 34 that cooperates with the shear ports 60 to form as suspension of individual cells in the liquid. In addition to this shearing action, the liquid and suspended cells are drawn upwardly into the inner bore 38 by the action of the rotating spiral portion 30. The upwardly traveling liquid suspension exit through the primary outlet openings 58 and, can continue upwardly and exit through the secondary outlet openings 54. By providing two sets of outlet openings 54, 58, complete exhaustion of the liquid suspension from the first chamber 79 is assured. In addition, the larger diameter secondary outlet openings 54 aid in insuring that all of the liquid suspension is exhausted from the first chamber 79. It will be appreciated that, because of the high rotational speed of the bit 16, the shearing and homogenizing action is accomplished in a short period of time. A typical sample of 10 ml can be extracted in about 10 seconds.

It is desirable to prevent any of the liquid and microorganism from entering the second chamber 78 to prevent damage to the air motor 12. As discussed previously, the flange 26 and collar 28 cooperate with the inner chamfer 76 to partially seal the second chamber 78 from the first chamber 79. This partial sealing acts to prevent any of the upwardly travelling liquid suspension from entering the second chamber 78. In addition, bleed air from the air motor 12 is permitted to enter the second chamber 78 and be exhausted through the vent outlets 48. The introduction of bleed air into the second chamber 78 acts to further prevent any of the upwardly travelling liquid and microorganisms from entering the second chamber 78. Thus, the combination of the bleed air and the sealing effect of the flange 26 and collar 28, as well as elimination of any capillary action, effectively prevents any of the liquid and microorganisms from entering the second chamber 78.

The bit 16 is maintained within the shroud 14 such that no portion of the bit 16 contacts any of the inner surfaces of the shroud 14. This elimination of any contact between the bit 16 and the shroud 14 prevents any heat build up due to friction that would normally occur in this type of device. The elimination of any heat due to friction is advantageous because no heat is then introduced into the sample. A typical sample of 10 ml, at room temperature when subjected to one full minute of blending action, experiences only about 1° C. increase in temperature. In addition, the elimination of friction between the bit 16 and the shroud 14 lengthens the operating life of both elements.

Thus, the dispersion tool 10 of the present invention provides a device that includes both a shear blade 34 to initially shear the clumps of cells of microorganisms in the sample liquid and a spiral portion 30 to further pump and disperse the cells to produce a homogenized dispersion of cells within the liquid. The tool 10 prevents the introduction of any substantial heat to the sample, which is advantageous. In addition, the tool 10, because of the lack of friction between the rotating parts, has a long useful life.

Although the invention has been described in detail with reference to a preferred embodiment, variations and modifications exist within the scope and spirit of the invention as described and defined in the following claims.

What is claimed is:

1. A dispersion apparatus for dispersing a material in a liquid comprising;

an elongated outer shroud having a first end and a second end and formed to include an inner bore, the shroud formed to include an axial inlet opening on the first end, a plurality of shear ports adjacent the first end, and at least one output intermediate the first end and the second end, elongated suspension means for finely dividing a material, said suspension means disposed within the inner bore and configured to rotate within the shroud, shearing means disposed on the suspension means and and located adjacent the shear ports and configured to cooperate with the shear ports to shear a portion of the material, and spiral means disposed on the suspension means axially above the shearing means and configured to cooperate with the inner bore to move a portion of the material and liquid axially upwardly through the inner bore and out of the inner bore through the at least one output opening.

2. The apparatus of claim 1, wherein said suspension means comprises an elongated shaft having a first end and a second end, the shaft being sized and configured to be received within said shroud inner bore.

3. The apparatus of claim 2, wherein said shearing means comprises a flattened shear blade formed on the first end of said shaft.

4. The apparatus of claim 3, wherein said spiral means comprises a portion of said shaft formed to include a spiral groove that is configured to urge the material and liquid upwardly between said shaft portion and said shroud inner bore upon rotation of said shaft within said inner bore in a first direction.

5. The apparatus of claim 2, wherein said shroud inner bore is formed to include a chamfer, the chamfer configured to separate said inner bore into a first chamber and a second chamber.

6. The apparatus of claim 5, further comprising an outwardly extending flange fixed to said elongated shaft, said flange configured to cooperate with said chamfer in said shroud inner bore to provide a partial fluid seal between said first chamber and said second chamber.

7. The apparatus of claim 6, wherein said second end of said elongated shaft is configured to receive a drive means for providing rotational movement to the shaft, the second end of the shaft and a portion of the drive means being located in said second chamber.

8. The apparatus of claim 7, further comprising means for introducing a fluid into said second chamber to increase the ambient pressure in the second chamber with respect to the ambient pressure in the first chamber.

9. A device for homogenizing the blending a liquid containing a plurality of suspended particles, the device comprising:

shroud means for channeling said liquid and suspended particles, the shroud means defining an inner bore that is formed to include an axial inlet opening, a plurality of shear ports adjacent the axial inlet opening, and at least one primary outlet opening axially spaced apart from the inlet opening and the shear ports, means disposed in the inner bore for homogenizing the liquid and suspended particles to form a liquid dispersion, the homogenizing means including shearing means located adjacent the shear ports, the shearing means configured to cooperate with the shear ports to shear a portion of the suspended particles, the homogenizing means also including spiral means for drawing liquid and suspended particles axially through the inner bore from the inlet opening to the at least one outlet opening.

10. The device of claim 9, wherein said homogenizing means comprises an elongated shaft having a first end and a second end and that is sized and shaped to be received in said shroud means inner bore.

11. The device of claim 10, wherein said shearing means comprises a shear blade fixed to said first end of said elongated shaft.

12. The device of claim 11, wherein said inner bore comprises first and second chambers, and said homogenizing means includes means for sealing the first chamber from the second chamber when the homogenizing means is disposed within the inner bore.

13. The device of claim 9, further comprising at least one secondary outlet opening formed in said shroud means and spaced axially apart from said at least one primary outlet opening.

* * * * *

UNITED STATES PATENT AND TRADEMARK OFFICE
CERTIFICATE OF CORRECTION

PATENT NO. : 4,745,068

DATED : May 17, 1988

INVENTOR(S) : Godfrey et al.

It is certified that error appears in the above-identified patent and that said Letters Patent is hereby corrected as shown below:

In column 1, line 14, replace "Products" with -- products --

In column 6, line 43, after "output" insert -- opening --.

Signed and Sealed this

Twentieth Day of December, 1988

*Attest:*

DONALD J. QUIGG

*Attesting Officer*

*Commissioner of Patents and Trademarks*